United States Patent [19]

Lezdey et al.

[11] Patent Number: 5,780,440
[45] Date of Patent: Jul. 14, 1998

[54] TREATMENT OF PULMONARY DISEASE WITH PROTEASE INHIBITORS

[75] Inventors: John Lezdey, Collingswood, N.J.; Allan Wachter, Tempe, Ariz.; Barry Starcher, Bullard, Tex.

[73] Assignee: Protease Sciences Inc., Voorhees, N.J.

[21] Appl. No.: 731,255

[22] Filed: Oct. 11, 1996

Related U.S. Application Data

[63] Continuation-in-part of Ser. No. 665,314, Jun. 17, 1996, abandoned.

[51] Int. Cl.$^6$ .......................... A61K 38/00; A61K 38/46
[52] U.S. Cl. .......................... 514/21; 514/8; 514/12; 514/921; 530/395; 530/397; 424/94.2; 424/94.64
[58] Field of Search .......................... 514/21, 81, 12, 514/921; 530/395, 397; 424/94.2, 94.64

[56] References Cited

U.S. PATENT DOCUMENTS

| | | | |
|---|---|---|---|
| 4,916,117 | 4/1990 | Lezdey et al. | 514/8 |
| 5,093,316 | 3/1992 | Lezdey et al. | 514/8 |
| 5,418,219 | 5/1995 | Ueda | 514/21 |

OTHER PUBLICATIONS

Gillissen et al, *J. Appl. Physiol.*, vol. 75, No. 2, pp. 825–832, 1993.

Temmesfeld–Wollbrück et al, *Lung*, vol. 173, No. 3, pp. 139–164, 1995.

Cross et al, *Infection and Immunity*, vol. 61, No. 7, pp. 2741–2747, 1993.

Fink et al, *Journal of Surgical Research*, vol. 49, No. 1, pp. 186–196, 1990.

Ohlsson et al, *Acta Paediatrica*, vol. 81, No. 10, pp. 757–759, 1992.

O'Donovan et al, *European Journal of Gastroenterology & Hepatology*, vol. 7, No. 9, pp. 842–852, 1995.

*Primary Examiner*—Cecilia J. Tsang
*Assistant Examiner*—Abdel A. Mohamed
*Attorney, Agent, or Firm*—John Lezdey

[57] ABSTRACT

The invention relates to methods and compositions for the prevention or treatment of patients suffering from respiratory distress syndrome and/or sepsis syndrome by administering directly into the lungs small or nicrocrystalline particles or droplets of at least one protease inhibitor alone or with an oxygen metabolite scavenger. The method can also include the treatment in combination with the monitoring of the urine desmosine level of the patients and the use of DNase.

10 Claims, No Drawings

TREATMENT OF PULMONARY DISEASE WITH PROTEASE INHIBITORS

RELATED APPLICATIONS

This application is a continuation-in-part of application Ser. No. 08/665,314 filed Jun. 17, 1996, now abandoned.

FIELD OF THE INVENTION

The present invention relates to compositions and methods of treating pulmonary abnormalities such as adult respiratory distress syndrome (ARDS), neonatal respiratory distress syndrome (RDS), and/or sepsis syndrome, and the prevention thereof. More particularly, the invention provides the treatment of patients by the treatment with protease inhibitors and/or oxygen metabolite scavengers directly into the lungs, particularly by aerosolization.

BACKGROUND OF THE INVENTION

The physiologic abnormalities that are characteristic of ARDS are largely due to the direct effects of collapsed and fluid-filled alveoli. In particularly, lung volumes are decreased and static lung compliance is reduced. Pulmonary vascular resistance is increased because of a) hypoxemic vasoconstriction, b) vascular occlusion from platelets, leukocytes or fibrin aggregates, or c) the presence of vasoactive inflammatory mediators.

The lungs of ARDS patients have capillaries which contain neutrophils, platelets and fibrin clots. The role of neutrophils in ARDS in substantial. The increased accumulation of neutrophils and their activation results in enhanced chemotaxis, release of neutrophil granules and generation of abnormally high levels of oxygen metabolites. Also many inflammatory cascades are activated and many interactions between pathways. Activation of complement, especially complement fragments $C3_a$ and $C5_a$ play a role between the initiating and the actual occurrence of alveolar injury. Cytokine release from mast cells and macrophages results in the presence of tumor necrosis factor (TNF-$\alpha$), elastase, endotoxin, complement $C5_a$, IL-1, cathepsin and platelet activating factors.

Partially reduced species of oxygen metabolites represent another group of agents that have been implicated as a cause of lung injury in humans with ARDS. Some of these agents are the result of high tensions of inspired oxygen so that there is also predisposition for sepsis syndrome. Cyclooxygenase synthetase, superoxide, $H_2O_2$ and myeloperoxidase by themselves or with other agents have been implicated in lung injury, for example, interstitial fibrosis. However, the combination of oxidants and proteases are more toxic to endothelial cells than either one alone.

"Sepsis syndrome" refers to the clinical condition in which patients with infection manifest severe, adverse systemic response, e.g., hypotension, or disseminated intravascular coagulation.

Since ARDS also involves non-pulmonary organs, treatment can also involve the injection or infusion of protease inhibitors.

The risks for subsequent development of ARDS is highest in pulmonary aspiration, diffuse intravascular coagulation, severe pneumonia, hypertransfusion, long bone or pelvic fractures, bacteremia, cutaneous burns and cardiopulmonary surgery.

Early intervention before ARDS or sepsis occurs is critical to a positive outcome and suggests that therapeutic treatment should occur prior to onset of the disease.

Neonatal respiratory distress syndrome (RDS) is commonly found in premature infants beginning a few hours after their birth. Premature infants are exposed to hyperoxia shortly after birth which causes an elastolytic activity imbalance with resulting toxic effects on lung parenchymal and vascular developments.

U.S. Pat. No. 5,093,316 to Lezdey et al, which is incorporated herein by reference, discloses the use of the aerosolization of alpha 1-antitrypsin in the treatment of pulmonary diseases where elastase and cathepsin G are involved.

U.S. Pat. No. 4,916,117 to Lezdey et al discloses the aerosolization of alpha 1-antichymotrypsin in the treatment of pulmonary diseases.

SUMMARY OF THE INVENTION

The present invention relates to methods and compositions for the prevention or treatment of inflammatory lung diseases such as RDS, ARDS and/or sepsis syndrome in patients. The method provides for the administration directly into the lungs an effective amount of a composition comprising a) at least one protease inhibitor capable of inhibiting the activation of inflammatory cascades and b) an oxygen metabolite scavenger. The composition is administered in particle form or droplets having a size of about 0.5 to 5 microns, preferably, less than 3 microns. The administration in adults and small children is preferably by aerosolization.

Advantageously the protease inhibitor is one which covalently but irreversibly binds with elastase. The protease inhibitor may be synthetic, natural, or a mutated recombinant protein.

It is preferred to monitor the disease as well as the administration of the compositions of the invention by monitoring the desmosine levels in the urine of the patients.

It is therefore an object of the invention to treat patients who may be susceptible to RDS, ARDS and/or sepsis syndrome or those who have acquired the disease. The treatment comprises administering directly into the lungs a composition comprising a protease inhibitor alone or in combination with an oxygen metabolite scavenger. Preferably, administration is performed by aerosolization.

It is a further object of the invention to monitor and treat pulmonary diseases by determination of desmosine levels in the urine of patients.

It is a still further object of the invention to monitor the ARDS patient by means of the desmosine level in their urine.

The term "microcrystalline" relates to particle of a size visible under an atomic force microscope which are either formed as particles or in a solution.

DESCRIPTION OF THE PREFERRED EMBODIMENTS

In accordance with the present invention a patient who is susceptible to RDS, ARDS or sepsis syndrome or one who has acquired the disease is treated by inhalation of a composition comprising a) a natural or synthetic protease inhibitor which is capable of inhibiting the activation of inflammatory cascades and b) an oxygen metabolite scavenger. The composition is administered in the form of particles or droplets having a particle size of about 0.5 to 5 microns, preferably less than 3 microns. A suitable inhalation device for administering droplets of the composition in the desired size is the PARI JET INHALER of the Pari Corporation.

In infants, aerosolization is not easily performed so that it may be necessary to administer the composition directly by droplets.

Protease inhibitors which are most suitable for use in the invention are the inhibitors which irreversibly bind with neutrophil elastase, for example, alpha 1-antitrypsin, alpha 2-macroglobulin and bronchial mucus inhibitor or those which bind tightly with neutrophil elastase and are slowly removed such as secretory leucocyte protease inhibitor.

Alpha 1-antitrypsin is most preferable of the protease inhibitors because it plays many roles in the treatment of the pulmonary diseases. Besides being a natural binder of neutrophil elastase, alpha 1-antitrypsin is known to inhibit the degranulation of lung mast cells, inhibit histamine release factors, inhibit the release of (TNF) tumor necrosis factor and inhibit the release of leukotriene $B_4$ from alveolar macrophages and mast cells.

Alpha 1-antichymotrypsin is particularly useful because it is a natural binder of cathepsin-G and superoxide. Consequently, alpha 1-antichymotrypsin has a multiple role in the treatment of pulmonary diseases since it deactivates a major oxygen metabolite which causes lung injury as well as deactivating alpha 1-antitrypsin and binds with cathepsin which also causes lung injury and is antibasophilic.

The preferred protease inhibitors are the native human proteins such as bronchial mucus inhibitor, alpha 1-antitrypsin, alpha 2-macroglobulin, alpha 1-antichymotrypsin, and secretory leucocyte protease inhibitor which do not attract antibodies so that they can be used over long periods of time. A combination of the protease inhibitors is most effective. However, where elastase is a major problem small molecule protease inhibitors which bind with elastase may be used. The low molecular weight inhibitors are preferably used with human deoxyribonuclease I.

The problems with utilizing low molecular weight protease inhibitors, namely, those less than 20,000 daltons is that they are not easily removed from the body after binding with elastase. However, the problem may be solved by also using DNase, especially, immediately after inhalation with the protease inhibitor.

Other inhibitors or stabilizers such as cromolyn or nedocronil sodium may be used adjunctively. However, it is essential that the compositions are administered in microcrystalline form, that is in the form of small particles or droplets having a particle size generally about 0.5 to 5 microns or smaller, preferably less than 3 microns.

The oxygen metabolite scavengers which can be used in the invention include ceruloplasmin, glutathione, glutathione peroxidase, superoxide dismutase, catalase and the like.

It has also been found that radioimmunoassay for desmosine is a valuable tool for use in the treatment of pulmonary diseases which are characterized by elevated elastase levels in the lungs. High levels of urine desmosine suggests that active elastin catabolism has occurred. The proteolysis that occurs in diseased lungs is caused by elastase released by pseudomonas aeruginosa and by degranulation of neutrophil releasing elastase and cathepsin G. During treatment with a protease inhibitor, there is an initial release of high levels of elastase-protease inhibitor complex and thereby a significant elevation of desmosine. The desmosine level decreases as the level of elastase in the lungs decreases. By comparison with desmosine levels of healthy persons in different age groups as well as those with diseased lungs, it is possible to detect the seriousness of the disease. After treatment with a protease inhibitor by inhalation therapy there is an initial rise in urine desmosine. The amount of desmosine decreases with continued use of the inhibitor. After discontinuance of the administration of the protease inhibitor, the desmosine level can revert to normal as compared with the standard or still be elevated through normal alpha 1-antitrypsin activity and elevated elastase in the lung. If the party is still suffering, a greater than normal rise of urine desmosine can be seen after renewed continuance of the treatment. This form of monitoring is most effective with infants to avoid invasive monitoring such as by bronchoalveolar lavage (BAL).

The active ingredients of the invention may be incorporated into a metered-dose aerosol unit containing a microcrystalline suspension of the drug in a mixture with propellants alone or with a carrier such as water or oleic acid. Preferred propellants are compressed air, trichloromonofluoromethane and dichlorodifluoromethane or mixtures thereof. Each unit may have a molecular proportion of active ingredient to the propellant between 3:1 and 3:2. Each actuation of the aerosol canister may deliver a quantity of drug equivalent to 42–90 mcg for multiple use daily.

It is preferred to generate aerosol droplets less than 3 microns in aerodynamic diameter using 4 ml of the composition at a concentration of about 25 mg/ml and wherein the nebulizer is driven by compressed air. A ratio of about 1:1 to about 3:1 of inhibitor to oxygen metabolite scavenger can be used. The administration is generally twice daily for the first week and then decreased as the disease decreases. The administration can take place prior to exposure to oxygen metabolite generation to avoid the onset of ARDS.

The PARI JET inhaler is useful for prophylactic use as well as for direct treatment of pulmonary diseases or inflammations. It can be used to administer the protease inhibitor and/or DNase.

The genetic form of emphysema and alpha 1-antitrypsin deficiency is currently being treated by infusion of a composition containing alpha 1-antitrypsin marketed by Miles Laboratories, Inc. under the trademark PROLASTIN. However, such form of administration delivers only about 2% of the drug to the lungs.

ARDS also results in the occurrence of the neutrophil cathepsin G and elastase release which cause destruction of the tissues. Alpha 1-antitrypsin only controls the elastase in such cases. It is also advisable to utilize other serine protease inhibitors such as alpha 1-antichymotrypsin which binds with cathepsin in order to obtain a broader spectrum of therapy for use in treatment and control of the disease. The administration of the useful serine protease inhibitors directly to the site of the disease, such as by inhalation, has been found to provide a rapid relief for the patient with a smaller drug requirement.

The following examples further illustrate the practice of this invention, but are not intended to be limiting thereof. It will be appreciated that the selection of actual amounts of specific alpha 1-antitrypsin or other serine protease inhibitors to be administered to any individual patient will fall within the discretion of the attending physician and will be prescribed in a manner commensurate with the appropriate dosages will depend on the patient's age, weight, sex, stage of disease and like factors uniquely within the purview of the attending physician.

EXAMPLE 1

To evaluate its potential for inhibiting neutrophil elastase in airways, a study of aerosolized PROLASTIN was performed using 100, 200 and 350 mg delivered by PARI LL nebulizer BID. Patients with PEV>60% of predicted were studied. They were not stratified by pre-treatment elastase activity. Sputum was obtained and BAL was performed at baseline and 12 hours after the last dose. The mean concentration of $\alpha_1$-PI in epithelial lining fluid (ELF) obtained by BAL increased from 3.78±0.68 µM (mean±SEM) to 13.29 ±1.75 µM (p<0.001) . In all patients except one, elastase activity decreased and/or the capacity to inhibit added exogenous elastase increased. Before Prolastin, the mean elastase activity in ELF was 5.10±1.59 µM. After PROLASTIN, the mean was an inhibitory capacity of 2.09±2.28 µM, a difference of 7.19 µM (p=0.003). There was a trend towards greater elastase inhibition at the higher doses of Prolastin (0.93 µM at 100 mg, 1.99 µM at 200 mg and 6.87 µM at 350 mg, p>0.1). Patients with the greatest change in elastase activity/inhibitory capacity (>15 µM) received 350 mg of drug. The mean concentration of elastase $\alpha_1$-PI complex in ELF increased from 1.48±0.18 µM before PROLASTIN to 2.54±0.41 µM after PROLASTIN (p=0.01). There was no significant change in the IL-8, total cells, or PMN in the ELF.

EXAMPLE 2

The procedure of Example 1 is followed expect that prior to aerosolization with alpha 1-antitrypsin the patients are aerosolized with 2.5 mg rh DNase (sold by Genentech under the trademark PULMOZYME).

There is improved clearance of airway obstruction and reduction of pseudomonas infection.

The use of DNase is particularly important to obtain protein clearance when lower molecular weight protease inhibitors are utilized.

It is apparent that when the disease is severe, DNase may be administered before and after inhalation with the protease inhibitors.

EXAMPLE 3

Seven men, 25–37 years old, were placed in a hyperbaric chamber and were given 100% oxygen at 2 atm for 12 h. Another group of 8 men (ages 28–35) were placed in the chamber and given 100% oxygen at 2.5 atm for 6 h. Twenty-four hour urine samples were collected 1 day prior to the study, during the exposure, and for 2 consecutive days following exposure.

Creatinine was measured using a kit (Gilford, Oberlin, Ohio, USA) according to the manufacturer's specifications. Urine was either assayed immediately or stored frozen at −20° C. until assayed.

The desmosine RIA was modified by attaching the antibody to magnetic particles. The desmosine antibody was affinity purified and attached to amine-terminated magnetic particles according to the manufacturer's instructions (PerSeptive Diagnostics, Cambridge, Mass., USA). The probe was made from labeled des-Bolton-Huriter with the following exceptions. Unbound was separated from the bound using a small column of Dowex-50 and diluted in 0.2M bis-tris propane buffer pH 7.6 containing 1.25% powdered DMEM (Sigma) to prevent nonspecific absorption. The sample was incubated in 200 µl of the probe (100.000 cpm) and 50 µl of the magnetic antibody (sufficient to bind 30–40% of the total counts) overnight and the bound separated from the unbound by placing the tubes in a Corning magnetic separating rack for 1 min. The rack was inverted to remove the unbound probe and the particles washed 3 additional times with 0.02M bis-tris propane buffer containing 0.02% Tween 20, allowing 1 min each time for the particles to stick to the magnets before inverting the rack.

Urine desmosine was expressed as picomoles per milligram creatinine. These values were converted to nanograms by multiplying by 0.526Assays were performed in duplicate on two separate days and the results averaged. Samples that varied by more than 10% between assays were repeated. The precision of the RIA was usually within 6–10% for both intra- and interassay variation. Whole, unhydrolyzed urine (50 µl) was assayed directly in the RIA or the sample was hydrolyzed and extracted as described previously [8].

The statistical significance of differences between means was tested using a two-tailed Student t test for unpaired data. Linear regression curves were calculated using the Mackintosh StatWorks package (Cricket Software, Inc., Philadelphia, Pa., USA).

The reproducibility and sensitivity of the magnetic antibody RIA was identical with the original desmosine RIA. Intra- and interassay variation were less than 10%. The use of antibody bound to magnetic particles significantly reduced the time required to perform the RIA. A bis-tris propane buffer was used for the assay since it is a stronger buffer in the 7.4 pH range. It was essential to add the powdered DMEM to the probe, which lowered the non-specific binding to 1% or less of the bound counts.

The desmosine RIA from whole, unhydrolyzed urine was compared to hydrolyzed urine that had been solvent extracted to remove cross-reacting substances for all the subjects in this study. With only a few exceptions, there was excellent agreement between desmosine values for whole unhydrolyzed urine and the extracted, hydrolyzed urine. Even when the absolute value for desmosine differed somewhat between whole and hydrolyzed urine, any change or trend in desmosine levels was mirrored by both procedures. This relationship between whole urine and hydrolyzed, solvent-extracted urine was true for all urines assayed in this study. The study showed that pulmonary diseases characterized by elevated elastase levels could be monitored by desmosine studies.

To more effectively treat the disease an oxygen metabolite scavenger could be used in a ratio of about 3:1 of the inhibitor to the oxygen metabolite scavenger. Glutathione has been found to be most effective.

EXAMPLE 4

An aerosol composition for administration by PARI JET was prepared by admixing.

200 mg of recombinant of alpha 1-antitrypsin 100 mg of glutathione 8 ml of water The composition is useful for the treatment of ARDS with a nebulizer capable of delivery of small particle or droplet size.

The same composition can be used to treat premature babies by direct administration to the lungs prior to incubation.

The same composition can be used to treat premature babies by direct administration to the lungs prior to incubation.

What is claimed is:

1. A method for the treatment of patients suffering from elevated elastase levels in airways such as respiratory distress syndrome which comprises the administration directly into the lungs an effective amount of a composition comprising particles or droplets of a) at least one protease inhibitor which inhibits the activation of inflammatory cascades in combination with b) an oxygen metabolite scavenger, said particle or droplets having a size of about 0.5 to 5 microns.

2. The method of claim 1 wherein said oxygen metabolite scavenger is selected from the group consisting of ceruloplasmin, glutathione, glutathione peroxidase, superoxide dismutase and catalase.

3. The method of claim 1 wherein said protease inhibitor is selected from the group consisting of bronchial mucus inhibitor, alpha 2-macroglobulin, alpha 1-antitrypsin, alpha 1-antichymotrypsin, secretory leukocyte protease inhibitor and combinations thereof.

4. The method of claim 1 wherein said protease inhibitor is a low molecular weight protease inhibitor.

5. The method of claim 1 wherein said patients have elevated elastase levels in the airways and DNase is administered.

6. The method of claim 1 wherein said particles or droplets have a size between 0.5 and less than 3 microns.

7. The method of claim 1 wherein said composition is administered by aerosolization as droplets.

8. The method of claim 1 wherein said composition is administered in particle form.

9. The method of claim 1 which comprises administering the combination of alpha 1-antitrypsin and glutathione.

10. The method of claim 1 further comprising monitoring desmosine level of the urine of said patient.

* * * * *